(12) United States Patent
Eckersall

(10) Patent No.: US 6,451,550 B1
(45) Date of Patent: Sep. 17, 2002

(54) HAPTOGLOBIN ASSAY

(75) Inventor: Peter David Eckersall, Glasgow (GB)

(73) Assignee: The University Court of the University of Glasgow, Glasgow (GB)

(*) Notice: Subject to any disclaimer, the term of this patent is extended or adjusted under 35 U.S.C. 154(b) by 0 days.

(21) Appl. No.: 09/554,363

(22) PCT Filed: Nov. 12, 1998

(86) PCT No.: PCT/GB98/03407

§ 371 (c)(1), (2), (4) Date: Jul. 12, 2000

(87) PCT Pub. No.: WO99/24833

PCT Pub. Date: May 20, 1999

(30) Foreign Application Priority Data

Nov. 12, 1997 (GB) ................................................ 9723773

(51) Int. Cl.[7] ............................. C12Q 1/28; C12Q 1/00; G01N 33/72
(52) U.S. Cl. ............................... 435/28; 435/4; 436/66; 436/64
(58) Field of Search ....................... 435/28, 4; 436/66, 436/67

(56) References Cited

U.S. PATENT DOCUMENTS 4,695,552 A * 9/1987 Schmitt et al.

FOREIGN PATENT DOCUMENTS

| | | | |
|---|---|---|---|
| EP | 0 448 072 A2 | 9/1991 | .......... G01N/33/72 |
| GB | 2 070 767 A | 9/1981 | .......... G01N/33/54 |
| JP | 04262796 | 9/1992 | ............ C12Q/1/28 |
| JP | 05005738 | 1/1993 | .......... G01N/33/53 |

OTHER PUBLICATIONS

Derwent abstract (Acc. No. 1991–283096) of JP 3003152 B2, 1991. Assay for free haemoglobin—using human haptoglobin bound to solid phase, peroxide reagent and colouring reagent.*

Derwent abstract (Acc. No. 1990–295057) of JP 02208568 A, 1990. Reagent kit for determination of haptoglobin—comprises aqueous solutions of 3, 3', 5, 5'-tetramethylbenzidine (deriv) and strontium—or hydrdrogen peroxide.*

Biosis abstract (1988:239782). Shim et al. (1987). Simple enzyme immunoassay for haptoglobin. Korean J Biochem 19(2): pp 77–82.*

* cited by examiner

Primary Examiner—Ralph Gitomer
Assistant Examiner—Mahreen Chaudhry
(74) Attorney, Agent, or Firm—Myers, Bigel Sibley & Sajovec

(57) ABSTRACT

The present invention relates to a haptoglobin assay of the type wherein the level of haptoglobin in a sample to be tested is determined by measuring the peroxidase activity of haptoglobin/haemoglobin complex. The assay employs at least one reagent for reducing a peroxidase effect due to any albumin or any other protein(s) present in the sample. The reagent may be selected from a) a reducing agent effective against disulphide bonds; b) a protein binding inhibitor and/or c) a chaotropic agent. The present invention also relates to kits suitable for use in such an asay.

18 Claims, No Drawings

HAPTOGLOBIN ASSAY

CROSS-REFERENCE TO RELATED APPLICATIONS

The present application is a U.S. national phase application of PCT International Application No. PCT/GB98/03407, having an international filing date of Nov. 12, 1998 and claiming priority to Great Britain Application No. 9723773.9 filed Nov. 12, 1997. The above PCT International Application was published in the English language and has International Publication No. WO 99/24833.

Haptoglobin (Hp) is a protein which is present in the blood of man and animals. The concentration of Hp in plasma or serum, following separation of the blood cells, varies in an individual animal and is related to the health status of the animal. Hp is one of a group of proteins the concentration of which increases dramatically following infection, inflammation or trauma. These proteins are known as the acute phase proteins.

Measurement of the concentration of Hp in plasma gives valuable diagnostic information to clinicians in human and veterinary medicine. In veterinary medicine, measurement of Hp is particularly important in assessing the health status of cattle and sheep as in these species Hp gives a particularly strong response to infection, with the concentration increasing in the circulation over 100 times. In other species, such as with man, the dog, the cat and the pig the measurement of Hp is also important as the plasma concentration increases 2 to 3 fold, which is sufficient to provide diagnostic information. Additionally in these other species a fall in Hp concentration may have value in diagnosis of haemolysis. Moreover, the measurement of Hp is of equal importance as a marker of inflammation or infection in laboratory animals such as rodents or mice.

Presently assays for Hp are based on either immunoassay or on the ability of Hp to bind to haemoglobin (Hb):

Hp in human plasma is measured in clinical biochemistry laboratories as a routine test for the acute phase response by antibody based methods with antiserum specific for human Hp. The commonest approach is by immunoturbidimetry, where the formation of a precipitate of antibody-Hp complex in solution can be measured and related to Hp concentration. However immunoturbidimetric assays are expensive when compared to routine biochemical tests as they require the preparation of a continuing supply of suitable antiserum. In addition, for use in veterinary diagnostic laboratories, tests based on antiserum to one species have to be validated for each separate species and the validation should be repeated for each new batch of antiserum used.

The original assays based on Hp-Hb binding depended on the finding that formation of the Hp-Hb complex alters the spectrophotometric absorption characteristic of Hb in proportion to the concentration of Hp in a plasma sample. But this has been replaced by making use of the innate peroxidase activity of the complex, which can be detected at a slightly acidic pH when it is proportional to the Hp content as the peroxidase activity of free haemoglobin is inhibited, allowing assays to be quantified by calibration with standard samples of Hp.

This assay is used in the majority of veterinary diagnostic laboratories which currently perform Hp assays and is preferred to immunoassay systems as it can be performed on all species with only a modest requirement for validation and it is also considerably cheaper than antibody based methods as the reagents are inexpensive. However, the automated version of this test utilises a reagent guaiacol which has a noxious odour and is not accepted by staff in many laboratories. The assay has not generally been adopted by commercial reagent suppliers probably for this reason. Attempts have been made to use other substrates for the peroxidase reaction, and while this can be achieved for manual methods, using tetra methyl benzidine (TMB), see Conner J. et al Research in Vet. Sci. (1988) 44, 82–88 a successful automated assay for Hp is still not available. This may be due to the sensitivity of TMB. It has been observed by the present inventors that serum samples without any haptoglobin (zero blanks) display a significant level of peroxidase activity capable of causing false positive results with TMB. It will be appreciated that such spurious peroxidase activity is undesirable when conducting an automated or semi-automated assay.

U.S. Pat. No. 4,695,552 describes a process for the determination of the Hp-Hb complex similar to the processes described above. However, it is identified that an acidic pH may not be sufficient to completely inactivate the peroxidase activity of free haemoglobin and that a detergent is added to substantially eliminate any peroxidase activity of the free haemoglobin. Nevertheless, there is no suggestion that components present in blood serum or plasma samples may effect the accuracy of such an assay.

It is amongst the objects of the present invention to obviate and/or mitigate at least one of the aforementioned disadvantages.

The present invention is based in part on the discovery by the present inventors that albumin and possibly other proteins present in blood samples has an undesirable "peroxidase effect" on assays of the type mentioned above.

The present invention therefore provides an assay for determining a level of haptoglobin in a sample, wherein the assay comprises the steps of:

a) forming a reaction mixture comprising the sample to be tested, haemoglobin and at least one reagent for reducing a peroxidase effect due to any albumin and/or any other protein(s) present in the sample, b) allowing the sample, haemoglobin and said at least one reagent to react, so as to allow formation of an haptoglobin/haemoglobin complex; and c) determining a level of peroxidase activity of said haptoglobin/haemoglobin complex, wherein the determination is carried out at an acidic pH sufficient to significantly reduce or substantially inactivate any peroxidase activity of uncomplexed haemoglobin.

It has been previously reported that uncomplexed haemoglobin displays a peroxidase activity at an acidic pH, but that this activity could be inactivated at pH 4.1. Makimura, S. and Suzuki, N. (1982) Jpn. J. Ven. Sci. 44, p15–21. U.S. Pat. No. 4,695,552 suggests however that a low level of peroxidase activity due to free haemoglobin may remain even at such a pH. Thus, the present assay is preferably carried out at a pH less than 4.1, for example pH 3.6–4.0, especially pH 3.8.

Typically the sample may be a blood sample generally of plasma or serum. The sample may be obtained from any animal, particularly mammalian animals, including rodentine, bovine, ovine, canine, feline, porcine and equine animals, as well as primates including humans. The sample may also be other body fluids such as milk, or ascitic fluid, or even in vitro incubation medium.

The sample may require to be diluted, if the haptoglobin concentration in the sample is above about 2 g/l, since the concentration of haptoglobin may not be accurately determined due to the non-linearity of a standard plot above such concentrations. However, the skilled addressee will readily understand that assay protocols could be developed with increased assay linearity to obviate any requirement for dilution. For example, a smaller sample volume may be used in appropriate circumstances.

The haemoglobin may be of the same origin as the animal from which the blood sample is being tested. That is, if the animal to be tested is bovine in origin, bovine haemoglobin may be employed. However, advantageously it has been found that the assay may be performed using haemoglobin of a species different from the species where the sample comes from. Thus the assay may be performed on a great variety of species while only utilising a single source of haemoglobin. Preferably also the haemoglobin is met-haemoglobin, although optionally oxy-haemoglobin may be used.

Serum and plasma from all species contains albumin, so this protein will be present in the sample to be tested at concentrations of up to 40 g/l. The present inventors have found through assessment of the best medium to use as a zero sample, for running as a blank, that there is significant interference with the assay from albumin. This interference has been detected at albumin concentrations of 1, 5, or 10% (10, 50, 100 g/l).

It has been observed that albumin does not have an innate peroxidase activity. Without wishing to be bound by theory it is thought that albumin and possibly other proteins present in blood serum, plasma or other samples to be tested may be binding to haemoglobin or possibly haematin released from the haemoglobin and preserving a peroxidase activity even at a pH (eg. pH 3.6–4.0) which would generally eliminate any free haemoglobin peroxidase activity. Moreover, this may be a reason why automated spectrophotometric assays for haptoglobin have hitherto not generally been adopted, due to the inability to obtain a zero level of peroxidase activity where haptoglobin is know to be absent. Previously this "peroxidase effect" may have inadvertently or accidentally been minimised due to a large dilution of the sample (eg. 500 fold) or by the use of an insensitive chromogen eg. guaiacol.

The present invention however reduces the requirement for a large dilution of the sample and allows more sensitive chromogens to be employed, by utilising at least one reagent for reducing a peroxidase effect due to any albumin or any other proteins present in the sample.

Said at least one reagent for reducing a peroxidase effect due to any albumin or any other protein(s) present in the sample may be independently selected from a) a reducing agent effective against disulphide bonds; b) a protein binding inhibitor and/or c) a chaotropic agent.

Preferably two or more of the above mentioned reagents are used to reduce any "peroxidase effect". However, the skilled addressee will appreciate that an excess of any of the above mentioned reagents will cause inhibition of the haptoglobin/haemoglobin reaction which must be avoided. For example assays performed utilising 8-anilino-1-naphthylene sulphonic acid (ANS) as the protein binding inhibitor and dithiothreitol as the reducing agent effective against disulphide bonds at concentrations of about 10 mmol/l and 4 mmol/l respectively result in almost complete inhibition of haptoglobin/haemoglobin complex peroxidase activity. Thus, the skilled addressee through appropriate controls may ensure that only the spurious "peroxidase effect" is reduced without substantially effecting the peroxidase activity of the haptoglobin/haemoglobin complex.

Conveniently the reducing agent effective against disulphide bonds may be dithiothreitol, dithioerythritol, cysteine, mercaptoethanol, glutathione, 4,4'-dithiodipyridine or 5,5'-dithio(2-nitrobenzoic acid).

Typically the protein binding inhibitor may be ANS, protoporphyrin, bilirubin, taurodeoxycholic acids (bile salts), dicoumarol or 2-mercaptobenzothiazole.

Typically the chaotropic agent may be guanidine hydrochloride, potassium thiocyanate or sodium chloride.

Preferably also a detergent is included in the assay. It was initially thought by the present inventors that the use of a detergent was important for reducing the peroxidase effect due to any albumin or other protein present in the sample. While a detergent may appear to have such an effect, it has now been observed that the use of a detergent may be important in ensuring that other components of the assay remain solubilised when conducting the assay. Moreover only low concentrations of detergent are preferred since it appears that high concentrations (eg. 25 g/l) increase the apparent peroxidase effect. Thus, preferably a detergent is added to the reaction mixture at a total concentration of less than 20 g/l, more preferably less than 10 g/l.

Typically the detergent may be a non-ionic surfactant such as polyoxyethylene sorbitol esters (eg. Tween 20, 40, 60, 80 etc.); polyoxyethylene-p-t-octyphenol (eg. Triton X-45, X-100, etc.); and/or polyoxyethylene (PEG) alcohols (eg. Brij 35, 36, etc.), or ionic surfactant such as sodium dodecyl sulphate, CHAPS and cetrimide.

Typically haptoglobin present in the sample and added haemoglobin are allowed to react for less than 20 mins, preferably less than 10 mins and most preferably less than 5 mins.

Once said haptoglobin/haemoglobin complex has formed it is possible to detect this by way of an innate peroxidase activity of the complex whereas free haemoglobin peroxidase activity is substantially inhibited by the acid pH of the assay. A level of peroxidase activity may then be correlated with a level of haptoglobin in a sample by reference to a standard curve genera ted using known concentrations of haptoglobin.

Typically said peroxidase activity may be detected by use of a chromogen and hydrogen peroxide wherein peroxidase activity results in a colour change of the chromogen which may be detected spectrophotometrically at a particular wavelength. Such peroxidase detection using chromogenic substrates is well known in the art for assaying haemoglobin levels, glucose levels and previously for haptoglobin levels when the influence of albumin on the assay was unknown, see for example Bauer, K. J. Clin. Chem. and Clin. Biochem. (1981) Vol. 19 pp971–976; Reijic, R. et al, Clin. Chem. (1992) Vol. 38 pp522–525 and Conner, J. G. and Eckersall, P. D. Research in Vet. Sci. (1988), 44, pp82–88.

As well as the chromogenic substrates mentioned in the above papers (ie. 4-amino phenozone, 2-amino-4-hydroxybenzenesulfonic acid (AHBS) and tetra methyl benzidine (TMB)), it will be immediately evident to one skilled in the art that other chromogenic substrates such as O-phenylene diamine dihydrochloride, O-dianisidine, Na-2-OH-3-5-dichlorobenzene-sulphonate, 2,2'-azino-di (3ethylbenzthiazoline-6-sulphonic acid (ABTS), 4-aminoantipyrine chromotropic acid optionally in co-reaction with 8, anilino-1-naphthylene sulphonic acid (ANS) and 4-iodophenol may be used in the present assay.

A preferred assay according to the present invention for determining a level of haptoglobin in a blood sample, comprises the steps of:

a) forming a reaction mixture comprising the sample to be tested, haemoglobin and a detergent, a reducing agent effective against disulphide bonds or a chaotropic agent and a protein binding inhibitor;

b) allowing the components of the mixture to react, so as to allow formation of an haptoglobin/haemoglobin complex; and c) determining a level of peroxidase activity of said haptoglobin/haemoglobin complex using a chromogenic substrate and spectrophotometric means, wherein the determination is carried out at an acidic pH sufficient to significantly reduce or substantially inactivate any peroxidase activity of uncomplexed haemoglobin.

A particularly preferred assay according to the present invention comprises the protein binding inhibitor/chromogenic co-reactant 8-anilino-1-naphthylene sulphonic acid (ANS) along with the chromogenic substrate 4-aminoantipyrine and phenol. It has been observed that ANS can supplement phenol in the co-oxidation reaction of hydrogen peroxide with 4-aminoantipyrine forming a blue chromogen which absorbs at 600 nm and has a greater absorbance than a red chromogen produced in the same conditions with phenol alone as co-reactant. Combination of ANS with 4-aminoantipyrine has been described previously for the determination of peroxide (see for example Chung et al, (1993), Talanta 40, p981–988).

The present invention also provides a kit for use in an haptoglobin assay according to the present invention wherein the kit comprises i) Haemoglobin;

ii) at least one reagent for reducing an effect any albumin may impart to the assay, wherein said at least one reagent is independently selected from a) a reducing agent effective against disulphide bonds, b) a protein binding inhibitor and/or c) a chaotropic agent; and iii) a chromogen for use in determining a level of peroxidase activity.

The kit may also comprise further components such as a buffer to maintain the desired pH for the assay, a detergent and/or standards of serum with known haptoglobin concentrations. It will be immediately evident to the skilled addressee that the components of the kit may be used to perform the haptoglobin assay with equipment such as test tubes or micro-titre plates and a spectrophotometer, as well as in automated biochemistry analysers as described herein.

The present invention will now be further described by way of reference to the following non-limiting examples.

EXAMPLE 1

Method for Automatic Determination of Haptoglobin Concentration using the Assay According to the Present Invention Reagents Stock Solutions 0.9% (w/v) NaCl (saline) Haemoglobin (Hb) stock solution at 30 g/l prepared according to Makimura and Suzuki (1982, *Jpn J Vet Sci*, 44 15–21) Chromogen citrate buffer: stock solution with 0.5 mol/l citrate buffer pH 3.8; 0.01% thiomersalate Working Solutions Hb working solution: Hb stock solution diluted 500 times in saline (50 $\mu$l diluted to 25 ml) Working chromogen buffer: the chromogen citrate buffer containing 20 mmol/l phenol; 1.6 mmol/l 4-aminophenazone (4-aminoantipyrine), 1 mmol/l 8-anilino 1-naphthalene sulphonic acid, 0.39 mmol/l dithioerythritol, 1% tween 20.

Substrate: Hydrogen peroxide ($H_2O_2$) add 100 $\mu$l of 30% $H_2O_2$ to 25 ml of $dH_2O$ Standard: serum with haptoglobin concentrations of 2.05 g/l diluted in 2% BSA to 1.03, 0,51, 0,125 and the 2% BSA as zero.

Samples: serum or plasma

Control samples: serum with known Hp concentration (high & low) repeated in each assay.

Calibration: once per day

Method for use on a MIRA (Roche Diagnostics Ltd) Analyser

Auto-analyser (MIRA) maintained at 37° C.

a) In the reagent rack, the diluted haemoglobin is the reagent (20 ml) working chromogen buffer is start reagent 1 (10 ml) and hydrogen peroxide is start reagent 2 (10 ml).

b) 7.5 $\mu$l of standard, sample or control is mixed with 200 $\mu$l of haemoglobin.

c) After 50s 90 $\mu$l of chromogen is added.

d) After a further 25s, 50 $\mu$l of substrate, ($H_2O_2$) is added and the increase in absorbance at 600 nm measured.

e) The difference in absorption over the next 50s is used to calculate results by comparison of absorbance change in standards to unknown sample.

The assay was linear to 2 g/l of haptoglobin, sufficient for most bovine & ovine samples. For other species, dilution may be required for samples above 2 g/l.

Results

Typical results are shown in Table 1 for a haptoglobin assay on the MIRA analyser with the complete chromogen solution described in the methods. A plot of the standard samples shows a linear relationship between the haptoglobin concentration and the change in absorbance at 600 nm (not shown).

The results also show the effectiveness of this chromogen solution in eliminating the effect of albumin, as both 5% BSA and foetal calf serum gave results which were <0.01 mg/ml. This may be compared to the results of Example 2 in which albumin binding was not eliminated.

TABLE 1

| Sample | mg/ml | Δ 600 nm | % of change in 2.05 Standard | Apparent Haptoglobin concentration mg/ml** |
|---|---|---|---|---|
| Haptoglobin | 2.05 | 1.0093 | 100 | |
| Standard | 1.03 | 0.5893 | 58 | |
| | 0.51 | 0.2745 | 27 | |
| | 0.12 | 0.0727 | 7 | |
| (2% BSA) | 0 | 0.0215 | 2 | |
| Saline | | 0.0211 | 2 | 0 |
| Foetal calf serum | | 0.0228 | 2 | <0.01 |
| 5% bovine serum albumin | | 0.0245 | 2 | <0.01 |

Two percent BSA was chosen as the medium to dilute the standards and to use as zero standard to provide a protein matrix for this dilution and this example confirms that when used as an assay blank it gave a minimal difference in change of OD when compared to saline, the difference being 0.004 absorbance units.

EXAMPLE 2

Using a Peroxidase Reagent without Inhibition of Albumin Binding

In order to show the effect albumin has on the assay, a comparative assay was performed in which the reagents (ie. ANS, dithioerythritol and tween 20) used to inhibit the effect of albumin were omitted.

In this example the assay was performed in a similar manner to that described for Example 1 except that the chromogen solution did not contain 8-anilino 1-naphthalene sulphonic acid, dithioerythritol or tween 20. The reagent contained phenol at 20 mmol/l and 4-aminophenazone (4-aminoantipyrine) at 1.6 mmol/l as the chromogen co-reactants, with absorbance read at 500 nm.
Result As shown in Table 2, there is a considerable effect of 5% albumin on the absorbance change, which would result in an erroneous reading of 0.59 mg/ml for the haptoglobin concentration if this assay had been used to quantify haptoglobin concentrations in a sample. Foetal calf serum also had a significant reaction and gave a positive result indicating falsely the presence of haptoglobin.

Note also that in this example the maximum change in absorbance was only 0.162 AU compared to 1.0093 AU when ANS was included as in example 1.

TABLE 2

| Sample | With PAP Δ 500 nm | % of change in Standard | Apparent Haptoglobin concentration mg/ml** |
|---|---|---|---|
| Haptoglobin Standard 2.05 mg/ml | 0.162 | 100 | |
| Saline | 0.003 | 1.9 | 0 |
| Foetal calf serum | 0.0104 | 6.4 | 0.14 |
| 5% bovine serum albumin | 0.0431 | 26.6 | 0.59 |

EXAMPLE 3

Haptoglobin Assay of the Present Invention in Diagnostic Use

Using the method described in Example 1, the haptoglobin concentration was determined in the serum from nine dairy cows suffering from mastitis, an infection of the udder which causes an acute inflammatory reaction. Twelve sera from dairy cows (from a study conducted in collaboration with Dr. J. L. Fitzpatrick, Department of Veterinary Clinical Studies, University of Glasgow Veterinary School) submitted to the laboratory but not suffering from inflammatory or infectious disease were also analysed for their haptoglobin concentration.

TABLE 3

Haptoglobin in dairy cattle with and without mastitis

| | n | mean | SD | median | range |
|---|---|---|---|---|---|
| Mastitis +ve | 9 | 0.84 | 0.29 | 0.80 | 0.4–1.32 |
| Mastitis −ve | 12 | 0.08 | .05 | 0.80 | 0.00–0.16 |

The mean haptoglobin concentration in the animals with mastitis was 10 times that in those without inflammatory conditions. The wide range of concentration found in the infected animals was due to samples coming from animals at different stages of infection, this could be from the peak of the acute phase or from the period during recovery.

The haptoglobin concentration was not 0 mg/ml in all of the samples from non infected animals and this is probably because, while inflammatory conditions were apparently absent the animals had sub-clinical conditions which gave a slightly raised concentration. It is possible that many or most animals outside pathogen free environments have such low levels of haptoglobin but further studies will be needed to clarify the levels encountered in normal populations. However the assay was effective in demonstrating an acute reaction to the mastitis.

EXAMPLE 4

Haptoglobin Assay without a Reagent for Reducing a Peroxidase Effect and with Detergent Only In order to assess the effect of detergent alone on the assay for haptoglobin in serum or in the presence of albumin a comparative assay was performed in which reagents were used to simulate the conditions recommended by Schmitt et al (U.S. Pat. No. 4,695,552). In this example an automated assay was performed on a MIRA analyser with modifications to the reagents and settings on the analyser.
Reagents Hb working solution: prepared from Hb stock solution as in Example 1.

Chromogen buffer: 0.1 mol/l sodium citrate pH 4.0; 0.5 mmol/l 2,2'-azino-di(3ethylbenzthiazoline-6-sulphonic acid) (ABTS); 3 g/l saponin.

Substrate: 32 mmol/l sodium perborate.

Standards: as in Example 1 except that standards were diluted in saline.

Control samples as in Example 1.

Method for use on MIRA (Roche Diagnostics Ltd) Analyser Auto-analyser maintained at 37° C.

a) In the reagent rack diluted Hb is the reagent (20 ml, ABTS/saponin chromogen is start reagent 1 (10 ml) and sodium perborate is start reagent 2 (10 ml).

b) 2.5 μl of standard, sample or control is mixed with 200 μl of Hb.

c) After 50s 90 μl of chromogen is added.

d) After a further 25s 20 μl of substrate (Na perborate) is added and the increase in absorbance at 405 nm measured.

e) The difference in absorption over the next 50s is used to calculate results by comparison of absorbance change in standards to those in control samples.

Results

TABLE 4

| Sample | mg/ml | Δ 405 nm | % of change in 2.05 standard | Apparent Haptoglobin concentration mg/ml** |
|---|---|---|---|---|
| Haptoglobin Standard | 2.05 | 1.0586 | 100 | |
| | 1.03 | 0.4790 | 45 | |
| | 0.51 | 0.2121 | 20 | |
| | 0.13 | 0.0442 | 4.2 | |
| Saline | 0 | 0.0155 | 1.5 | |
| 2% BSA | | 0.1639 | 15 | 0.31 |
| 5% BSA | | 0.3730 | 35 | 0.72 |
| Foetal calf serum | | 0.0353 | 3.3 | 0.07 |

As shown in Table 4, there is considerable effect of bovine serum albumin at both 2 and 5% (w/v) on the absorbance change of this chromogen/detergent system and erroneous results of 0.31–0.72 mg/ml of haptoglobin would be reported for serum samples containing 20–50 g/l of albumin but no haptoglobin. The reference range for albumin in most species is in the order of 25–40 g/l for albumin and therefore an assay for haptoglobin is preferably not substantially affected by such concentrations of albumin.

EXAMPLE 5

Haptoglobin Assay without a Reagent for Reducing a Peroxidase Effect and Increased Detergent Concentration Haptoglobin in serum or plasma was examined by performing the assay as in example 4 (ABTS as chromogen) except that the concentration of saponin was increased to 25 g/l. The results are shown in Table 5.

TABLE 5

Absorbance of reactions with Saponin at 25 g/l

| Sample | mg/ml | Δ 405 nm | % of change in 2.05 standard | Apparent Haptoglobin concentration mg/ml** |
|---|---|---|---|---|
| Haptoglobin | 2.05 | 0.3763 | 100 | |
| Standard | 1.03 | 0.1764 | 47 | |
| | 0.51 | 0.0551 | 15 | |
| | 0.13 | 0.04887 | 13 | |
| Saline | 0 | 0.0417 | 11 | |
| 2% BSA | | 0.2482 | 66 | 1.31 |
| 5% BSA | | 0.6363 | 169 | >2 |
| Foetal calf serum | | 0.0873 | 23 | 0.52 | with saponin increased to 25 g/l there was a marked increase in the albumin effect with the changes in absorbance with 2 & 5% albumin resulting in apparently high levels of haptoglobin.

EXAMPLE 6

Haptoglobin Assay of the Present Invention in the Absence of Detergent

The method described in Example 1 was used except that detergent such as Tween 20 was omitted from the reagent mixture, the sample volume was 2.5 μl and the volume of the hydrogen peroxidase reagent was 20 μl.

TABLE 6

Change in absorbance at 600 nm without detergent

| Sample | mg/ml | Δ 600 nm | % of change in 2.05 standard | Apparent Haptoglobin concentration mg/ml** |
|---|---|---|---|---|
| Haptoglobin | 2.05 | 0.374 | 100 | |
| Standard | 1.03 | 0.2157 | 57 | |
| | 0.51 | 0.1456 | 39 | |
| | 0.13 | 0.0928 | 25 | |
| Saline | 0 | 0.0461 | 12 | |
| 2% BSA | | 0.0874 | 23 | 0.09 |
| 5% BSA | | 0.0999 | 27 | 0.18 |
| Foetal calf serum | | 0.0858 | 23 | 0.09 |

In the absence of detergent the albumin effect was apparent to a small extent with the change in absorbance at 600 nm being greater in the 2 & 5% albumin and foetal calf serum than in the sample of saline alone. Visual inspection of the reaction cuvettes after the reaction revealed that precipitation had occurred in all reaction mixtures. This was reflected in the absorbance readings at 75 sec which was similar in each cuvette and was on average four fold greater than in the reaction taking place in the presence of Tween 20 (Table 7).

TABLE 7

Average absorbance at 600 nm of cuvettes after 75 seconds of reaction

| Reaction mixture | Chromogen with detergent | Chromogen without detergent |
|---|---|---|
| Mean OD 600 nm at 75 sec (range) | 0.0693 (0.0683– 0.0717) | 0.2423 (0.1870– 0.3151) |

The absorbance reading at 75 sec is taken immediately after addition of the chromogen solution to the mixture of sample plus haemoglobin and immediately prior to addition of hydrogen peroxide. It is apparent that the mixing of chromogen solution with the haemoglobin solution causes a precipitation to occur which can be prevented by the presence of detergent such as Tween 20 and there was considerable variation in the effect of the precipitate on the absorbance with a range of 0.1870 to 0.3151. The precipitation occurred even when the sample is saline and these findings indicate that detergent may be required for the assay of haptoglobin to maintain solubility of reagents.

EXAMPLE 7

Haptoglobin Assay of the Present Invention in Experimental Use

Using the method described in Example 1, the haptoglobin concentration was determined in the serum of rats which were part of an experimental investigation of the pathogenicity of *Bordetella pertussis* bacteria (whooping cough) (from a study in collaboration with Dr. R. Parton, Institute of Biomedical and Life Sciences, University of Glasgow). Eight days after infection serum was collected from six infected rats (Sprague-Dawley) and from six uninfected controls and were stored at −20° C. before analysis using the haptoglobin assay.

TABLE 8

Haptoglobin in rats infected with *B pertussis* and in uninfected control rats

| Group | n | mean | SD |
|---|---|---|---|
| infected rats | 6 | 1.81 | 0.79 |
| uninfected rats | 6 | 0.39 | 0.10 |

The haptoglobin concentration as determined by the assay described in Example 1 was increased by a factor of over four times following infection with *B pertussis* which demonstrates the use of the assay for haptoglobin in experimental studies of the host response to infection.

EXAMPLE 8

Method for Automatic Determination of Haptoglobin Concentration using a Chaotropic Agent to Replace a Disulphide Bond Reducing Agaent The method was performed on a MIRA analyser as in Example 1 except that the Hb working solution was prepared in saline containing 0.5 mol/l quanidine hydrochloride, the working chromnogen buffer was the citrate buffer containing 20 mmol/l phenol; 1.6 mmol/l 4-aminophenazone (4-aminoantipyrine); 1 mmol/l 8-anilino 1 naphthalone sulphonic acid; 1% tween 20, (ie. the dithiecrythritol was omitted) and the sample volume was 2.5 µl.

TABLE 9

| Sample | mg/ml | Δ 600 nm | % of change in 2.05 standard | Apparent Haptoglobin concentration mg/ml** |
|---|---|---|---|---|
| Haptoglobin Standard | 2.05 | 0.2438 | 100 | |
| | 1.03 | 0.1180 | 48 | |
| | 0.51 | 0.0568 | 23 | |
| | 0.13 | 0.0174 | 7.1 | |
| Saline | 0 | 0.0102 | 4.1 | 0 |
| 2% BSA | | 0.0106 | 4.3 | 0 |
| 5% BSA | | 0.0116 | 4.7 | 0.01 |
| Foetal calf serum | | 0.0122 | 5.0 | 0.01 |

The result demonstrates that a chaotropic agent such as guanidine hydrochloride can be used to inhibit the albumin effect on peroxidase activity and that albumin up to 2% does not effect the assay, while up to 5% there is only a marginal effect.

What is claimed is:

1. An assay for determining a level of haptoglobin in a sample, wherein the assay comprises the steps of:
   a) forming a reaction mixture comprising the sample to be treated, haemoglobin and at least one reagent for reducing a peroxidase effect due to any albumin and/or any other protein(s) present in the sample other than albumin, wherein the at least one reagent for reducing a peroxidase effect is selected from the group consisting of a) a reducing agent effective against disulphide bonds; (b) a protein binding inhibitor, c) a chaotropic agent, and d) combinations thereof;
   b) allowing the sample, haemoglobin and said at least one reagent to react, so as to allow formation of an haptoglobin/haemoglobin complex;
   c) determining a level of peroxidase activity of said haptoglobin/haemoglobin complex, wherein the determination is carried out at an acidic pH sufficient to significantly reduce or substantially inactivate any peroxidase activity of uncomplexed haemoglobin; and
   d) correlating the level of peroxidase activity with the level of haptoglobin in the sample.

2. The assay according to claim 1 wherein the assay is carried out at a pH between pH 3.6 to 4.0.

3. The assay according to claim 1 wherein the sample is a blood sample.

4. The assay according to claim 3 wherein the blood sample is a sample of plasma or serum.

5. The assay according to claim 1 wherein the sample is milk, ascitic fluid or in vitro incubation medium.

6. The assay according to claim 1 wherein two or more of said reagents are used.

7. The assay according to claim 1 wherein the reducing agent effective against disulphide bonds is independently selected from dithiothreitol, dithioerythritol, cysteine, mercaptoethanol, glutathione, 4,4'-dithiodipyridine, or 5,5'-dithio(2-nitrobenzoic acid).

8. The assay according to claim 1 wherein the protein binding inhibitor is independently selected from 8-anilino-1-naphthylene sulphonic acid (ANS), protoporphyrin, bilirubin, taurodeoxycholic acids (bile salts), dicoumarol, or 2-mercaptobenzothiazole.

9. The assay according to claim 1 wherein the chaotropic agent is independently selected from guanidine hydrochloride, potassium thiocyanate or sodium chloride.

10. The assay according to claim 1 further comprising a detergent.

11. The assay according to claim 10 wherein the detergent is added to the reaction mixture at a total concentration of less than 20 g/l.

12. The assay according to claim 10 wherein the detergent is selected from a non-ionic surfactant selected from the group consisting of polyoxyethylene sorbitol esters; polyoxyethylene-p-t-octyphenol; polyoxyethylene (PEG) alcohols, and mixtures thereof, or an ionic surfactant selected from the group consisting of sodium dodecyl sulphate, CHAPS, and cetrimide, and mixtures thereof.

13. The assay according to claim 1 wherein the peroxidase activity is detected by use of chromogen and hydrogen peroxide wherein peroxidase activity results in a colour change of the chromogen which may be detected spectrophotometrically at a particular wavelength.

14. The assay according to claim 13 wherein the chromogenic substrate is selected from 4-amino phenozone, 2-amino-4-hydroxybenzenesulfonic acid, tetra methyl benzidine, O-phenylene diamine dihydrochloride, O-dianisidine, Na-2-OH-5-dichlorobenzene-sulphonate, 2,2'-azino-di (3ethylbenzthiazoline-6-sulphonic acid (ABTS) 4-aminoantipyrine chromotropic acid optionally in co-reaction with 8-anilino-1-naphthylene sulphonic acid (ANS) and 4-iodophenol.

15. An assay for determining a level of haptoglobin in a sample, comprising the step of:
   a. forming a reaction mixture comprising the sample to be treated, haemoglobin, and a detergent, a reducing agent effective against disulphide bonds or a chaotropic agent and a protein binding inhibitor;
   b. allowing the components of the mixture to react so as to allow formation of an haptoglobin/haemoglobin complex;
   c. determining a level of peroxidase activity of said haptoglobin/haemoglobin complex using a chromogenic substrate and spectrophotometric means, wherein the determination is carried out at an acidic pH sufficient to significantly reduce or substantially inactivate any peroxidase activity of uncomplexed haemoglobin; and
   d. correlating the level of peroxidase activity with the level of haptoglobin in the sample.

16. The assay according to claim 15 comprising the protein binding inhibitor/chromogenic co-reactant 8-anilino-1-naphthylene sulphonic acid (ANS) and the chromogenic substrate 4-aminoantipyrine and phenol.

17. A kit for use in an haptoglobin assay, wherein the kit comprises;
   i) Haemoglobin for forming a haptoglobin/haemoglobin complex;
   ii) at least one reagent for reducing a peroxidase effect any albumin and/or other protein(s) may impart to the assay, wherein said at least one reagent is selected from the group consisting of a) a reducing agent effective against disulphide bonds, b) a protein binding inhibitor, c) a chaotropic agent, and d) combinations thereof; and
   iii) a chromogen for use in determining a level of peroxidase activity of said heptoglobin/haemoglobin complex.

18. A kit according to claim 17 further comprising a detergent.

* * * * *